US008902428B2

(12) United States Patent
Schlezinger et al.

(10) Patent No.: US 8,902,428 B2
(45) Date of Patent: Dec. 2, 2014

(54) PROCESS AND APPARATUS FOR MEASURING THE CRYSTAL FRACTION OF CRYSTALLINE SILICON CASTED MONO WAFERS

(75) Inventors: Asaf Schlezinger, Sunnyvale, CA (US); Amir Al-Bayati, San Jose, CA (US)

(73) Assignee: Applied Materials, Inc., Santa Clara, CA (US)

( * ) Notice: Subject to any disclaimer, the term of this patent is extended or adjusted under 35 U.S.C. 154(b) by 178 days.

(21) Appl. No.: 13/421,194

(22) Filed: Mar. 15, 2012

(65) Prior Publication Data

US 2013/0242287 A1    Sep. 19, 2013

(51) Int. Cl.
*G01N 21/55* (2014.01)

(52) U.S. Cl.
USPC ............................. 356/445; 356/51; 356/237.2

(58) Field of Classification Search
USPC .......... 356/237.1, 239.1–239.3, 239.7, 239.8, 356/237.2–237.6, 432–435, 445, 446, 51; 382/142, 145, 147
See application file for complete search history.

(56) References Cited

U.S. PATENT DOCUMENTS

| 5,136,624 | A  | * | 8/1992  | Schneider et al. ............... 378/73 |
| 5,197,105 | A  | * | 3/1993  | Uemura et al. ................. 382/147 |
| 5,573,680 | A  |   | 11/1996 | Shaw et al. |
| 6,295,335 | B1 | * | 9/2001  | Cossard ....................... 378/98.12 |
| 6,657,708 | B1 |   | 12/2003 | Drevillon et al. |
| 6,713,371 | B1 |   | 3/2004  | Gu |
| 7,195,992 | B2 |   | 3/2007  | Gu et al. |
| 7,227,188 | B2 |   | 6/2007  | Gu |
| 7,345,746 | B2 |   | 3/2008  | Takami |
| 7,361,578 | B2 |   | 4/2008  | Gu |
| 7,663,383 | B2 |   | 2/2010  | Chen et al. |
| 8,605,858 | B2 | * | 12/2013 | Singh et al. ...................... 378/73 |
| 2007/0105352 | A1 |   | 5/2007  | Gu et al. |
| 2007/0169684 | A1 | * | 7/2007  | Stoddard ........................ 117/13 |
| 2007/0247618 | A1 | * | 10/2007 | Graf et al. ................... 356/237.5 |
| 2007/0263206 | A1 | * | 11/2007 | LeBlanc et al. ............ 356/239.7 |
| 2010/0051098 | A1 | * | 3/2010  | Sheng et al. .................. 136/256 |
| 2010/0067010 | A1 |   | 3/2010  | Sakai et al. |
| 2010/0197051 | A1 | * | 8/2010  | Schlezinger et al. ........... 438/16 |
| 2010/0253942 | A1 |   | 10/2010 | Mack et al. |
| 2011/0033957 | A1 | * | 2/2011  | Holden et al. .................. 438/16 |
| 2011/0268344 | A1 | * | 11/2011 | Chan ............................ 382/145 |
| 2013/0100275 | A1 | * | 4/2013  | DeGreeve et al. .............. 348/87 |

FOREIGN PATENT DOCUMENTS

JP           2003318240         11/2003

OTHER PUBLICATIONS

PCT Search Report and Written Opinion in PCT/US2013/031452 dated Jun. 28, 2013, 14 pgs.
PCT International Preliminary Report on Patentability in PCT/US2013/031452, mailed Sep. 25, 2014, 11 pages.

* cited by examiner

*Primary Examiner* — Tarifur Chowdhury
*Assistant Examiner* — Michael P Lapage
(74) *Attorney, Agent, or Firm* — Servilla Whitney LLC

(57) ABSTRACT

Provided are methods and apparatus for determining the crystal fraction of a casted-mono silicon wafer. A light source is directed at the wafer and the transmission or reflection is measured by a detector. An image of the wafer is generated by a processor and the crystal fraction is calculated from the generated image. The crystal fraction is correlated to the efficiency of the solar cell produced, allowing for the rejection of inferior wafers prior to processing.

19 Claims, 6 Drawing Sheets

PROCESS AND APPARATUS FOR MEASURING THE CRYSTAL FRACTION OF CRYSTALLINE SILICON CASTED MONO WAFERS

BACKGROUND

Embodiments of the invention generally relate to methods and apparatus for measuring the crystal fraction of crystalline silicon casted mono wafers. More specifically, embodiments of the invention are directed to methods and apparatus for measuring the crystal fraction of the wafer by one or more of transmitting near infrared light through the wafer and reflecting light off of the surface of the wafer and evaluating the determining the percent mono-crystalline surface area.

The two main types of bulk material used in solar cell technologies are monocrystalline and polycrystalline silicon. Monocrystalline wafers are relatively expensive, but produce more efficient solar cells. On the other end, polycrystalline wafers are cheaper to produce, but result in lower efficiency cells. Recently, a new technology named Casted-Mono (AKA Quasi-Mono) was introduced and has quickly gained traction. Casted-Mono produces solar wafers that are both efficient and low cost to manufacture.

The new process for casted-mono, suffers from high variation in quality, or more specifically-variation in mono crystal area of the wafers. Quality distribution of the crystal fraction (CF) correlates with high distribution of the expected efficiency of the solar cells to be manufactured out of these wafers.

Therefore, it is important to develop a method of inspecting the as-cut wafers and determine the crystal fraction. This information can be used to sort and grade the manufactured wafers and can also provide real time feedback on the manufacturing process. Currently there are no commercial inspection systems to measure the CF, and feedback on wafers' quality can be obtained only after the cell is 100% manufactured. Therefore, there is a need in the art for methods and systems to accurately and repeatedly measure the crystal fraction.

SUMMARY

One or more embodiments of the invention are directed to methods of determining a crystal fraction of a casted-mono wafer. Light is passed through the casted-mono silicon wafer. The light that has passed through the wafer is detected and an image is created of the casted-mono silicon wafer from the detected light. The crystal fraction of the casted-mono wafer is determined.

In some embodiments, the light comprises near infrared light. In one or more embodiments, the near infrared light has a wavelength of about 870 nm. In some embodiments, the light is emitted by a light emitting diode (LED).

In some embodiments, determining the crystal fraction of the casted-mono wafer comprises determining the largest area of the wafer that is mono-crystalline. One or more embodiments further comprise determining the percentage of mono-crystalline wafer area. Some embodiments further comprise evaluating the casted-mono wafer quality based on the percentage of mono-crystalline wafer area. In one or more embodiments, a mono-crystalline wafer are greater than 90% indicates a good wafer, a percentage in the range of about 60% to about 90% indicates a second grade wafer and a percentage less than about 60% indicates a poor wafer.

Additional embodiments of the invention are directed to methods of determining a crystal fraction of a casted-mono silicon wafer. The casted-mono silicon wafer is contacted with light. The light that has one or more of passed through the wafer and reflected off of the wafer is detected. An image is created of the casted-mono silicon wafer from the detected light and the crystal fraction of the casted-mono silicon wafer is determined.

In some embodiments, the light is near infrared light having a wavelength of about 870 nm and is passed through the casted-mono silicon wafer. In some embodiments, the light is one or more of ultraviolet light, visible light and infrared light and is reflected off of the surface of the casted-mono silicon wafer.

In some embodiments, determining the crystal fraction of the casted-mono crystalline silicon wafer comprises determining the largest area of the wafer that is mono-crystalline and calculating the percentage of mono-crystalline wafer area.

Further embodiments of the invention are directed to systems for measuring crystal fraction in casted-mono wafers. The systems comprise a support, a light source, a detector and a processor. The support holds a casted-mono wafer. The light source emits light directed at the casted-mono wafer. The detector measures the light after exposure to the casted-mono wafer. The processor is in communication with the detector and evaluates the crystal fraction of the wafer.

In some embodiments, the light is near infrared light. In some embodiments, the near infrared light is directed to a back side of the casted-mono wafer and the detector measures near infrared light transmitted through the casted-mono wafer from the light source. In some embodiments, the near infrared light has a wavelength of about 870 nm. In one or more embodiments, the light source is a light emitting diode (LED). In some embodiments, the light is one or more of ultraviolet, visible and infrared light.

In some embodiments, the light is directed to a front side of the casted-mono wafer and the detector measures the light reflected from the front side of the casted-mono wafer from the light source.

In some embodiments, the processor evaluates the crystal fraction of the wafer by comparing the area of the wafer with relatively uniform transmission to the area of relatively non-uniform transmission and determining a percentage of uniform area.

BRIEF DESCRIPTION OF THE DRAWINGS

So that the manner in which the above recited features of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention relate to crystalline silicon solar cells and wafer manufacturing as a fast and reliable way to measure the crystal fraction of casted mono wafers at the stage where they enter the cell manufacturing line or leave the wafering process (as bare wafers). The crystal fraction is correlating with the end cell efficiency. Therefore, this is a very important parameter that helps predict and estimate the quality of the raw material before processing it. Manual screening is used to test the quality of the raw materials which is not a very accurate or repeatable process. Additionally, manual screening does not meet the throughput requirements for manufacturing.

Embodiments of the methods provide extremely accurate and repeatable measurements of the crystal fraction, providing valuable data in real time. The methods and system have the potential to be widely adopted as an industry standard for CF inspection and yield improvement.

In some embodiments, the wafers are being scanned with an imaging Near Infra Red (NIR) vision system in transmission mode that produces a clear and contrast image showing the wafer's morphology. All grain boundaries are clearly seen by this technique, which uses a line scan imaging, in order to obtain a fast on-the-fly image. The software that is used for processing the image finds the largest area on the wafer that is smooth, ranking it as the wafer's mono crystal area. This fraction out of the entire wafer's area is regarded as the crystal fraction, and gives the important data to the cell manufacturer or the wafer manufacturer about the quality of the material.

Figure 1:
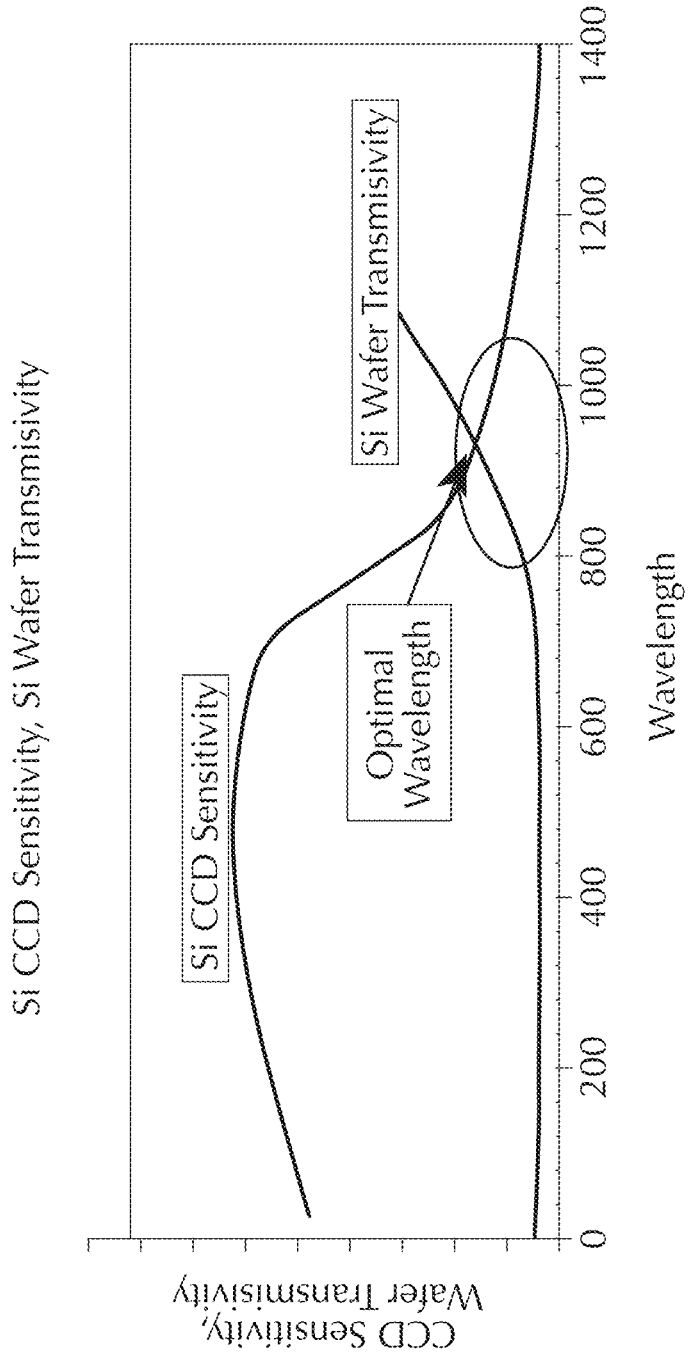
FIG. 1 shows a graph of the transmittance of a silicon wafer and a silicon CCD detector sensitivity.

One or more embodiments of the inspection system are based on bright field transmission optics in the NIR wavelengths. Light shines through the wafer and creates an image on a CCD camera. Relying on the fact that the silicon material is semitransparent in near infrared light, a linear 1D LED light source has been selected and placed under the conveyor carrying the wafer. The exact wavelength of the light source has been determined by taking into account the transmission spectrum of the silicon wafer and the responsivity spectrum of the silicon CCD sensor, as shown in FIG. 1. While the following description refers to silicon wafers, it will be understood by those skilled in the art that other wafer materials can be tested and the scope of the invention should not be limited to silicon wafers only.

Figure 2:
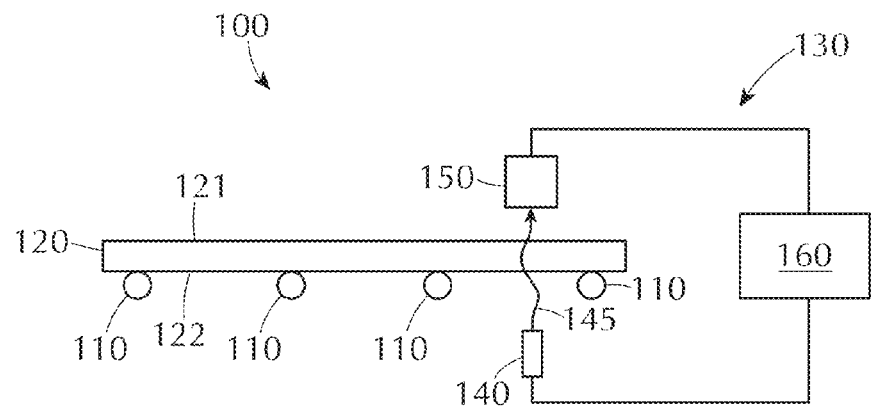
FIG. 2 shows a schematic of a system in accordance with one or more embodiments of the invention.

FIG. 2 shows a schematic representation of a system 100 in accordance with one or more embodiments of the invention. The system 100 includes a support 110 that holds the casted-mono silicon solar wafer 120. The support 110 can be, for example, a conveyer, lift pins or an air bearing system. The support 110 should not interfere with the transmission or detection of light used by the system. The embodiment shown in FIG. 2 illustrates a conveyer as the support 110 and is shown as a series of circles. The wafer 120 is moved along the conveyer through the vision system 130.

In the embodiment shown in FIG. 2, the wafer 120 is moved while the vision system 130 remains stationary. This is merely illustrative of one possible system and should not be taken as limiting the scope of the invention. In some embodiments, the wafer 120 remains stationary and the vision system 130, or a portion of the vision system, is moved across the wafer 120.

The vision system 130 includes a light source 140 that emits light 145 directed at the casted-mono silicon solar wafer 120. The light source 140 in FIG. 2 is shown below the wafer 120 with the light 145 passing through the wafer 120. The light source 140 in this embodiment directs light 145 at the back surface 122 of the wafer 120. The light 145 passes through the wafer 120 and is detected by detector 150 which is directed at the front side 121 of the wafer 120. This is an embodiments using light transmission through the wafer 120. Those skilled in the art will understand that this is merely one possible arrangement and that this should not be taken as limiting the scope of the invention.

The light source 140 can be any suitable light source depending on the mode of measurement (i.e., transmission or reflection). Suitable light sources emit radiation in one or more of the visible, ultraviolet, infrared and near infrared wavelength regions. In some embodiments, as may be useful with transmission measurements, the light source 140 emits near infrared light 145. The near infrared light 145 is directed at the back side 122 of the wafer 120 and the detector 150 measures the near infrared light transmitted through the wafer 120. In the transmission mode of FIG. 2, the light source 140 may emit light at any suitable wavelength that can pass through the wafer 120. In one or more embodiments, the wavelength is one or more of 870 nm or 950 nm. In some embodiments, the wavelength is in the range of about 870 nm to about 950 nm. In one or more embodiments, the wavelength is in the range of about 800 nm to about 1000 nm. The light source 140 can be any type of light source including, but not limited to, lasers, light emitting diodes (LEDs), organic light emitting diodes (OLEDs), atomic line sources, neon lamps, mercury-vapor lamps gas discharge lamps and sodium lamps.

Figure 3:
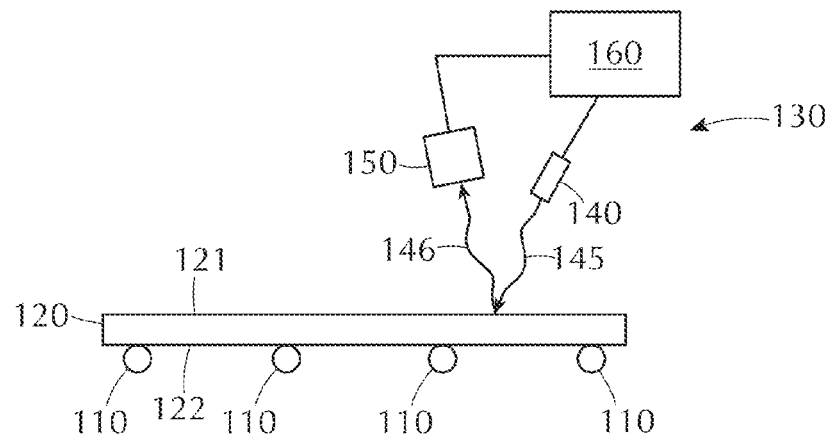
FIG. 3 show a schematic of a system in accordance with one or more embodiments of the invention.

In the embodiment shown in FIG. 3, the vision system is arranged to make reflectance measurements of the front surface 121 of the wafer 120. Here, the light source 140 directs light 145 at the front surface 121 of the wafer 120, which is reflected to form reflected light 146. The light 145, also called incident light, contacts the wafer 120 and, at least a portion, is reflected. The reflected light 146 is detected by detector 150. The reflected light 146 can be the result of specular reflectance or diffuse reflectance.

In the embodiment of FIG. 3, the light 145 is directed at the front side 121 of the casted-mono silicon solar wafer 120. The detector 150 measures the reflected light 146 from the front side 121. The light source of some embodiments is one or more of visible and ultraviolet light. Depending on the specific makeup of the wafer 120, the visible and ultraviolet light will not be transmitted through the wafer 120, but will be reflected, at least partially, toward the detector.

The detector 150 can be any suitable detector for measuring light. Suitable detectors include, but are not limited to, line scan cameras and charge-coupled devices (CCDs). In some embodiments, the detector is a line scan camera which can detect light of the wavelength emitted by the light source 140.

A processor 160 is in communication with the detector 150 and can evaluate the data provided by the detector. In some embodiments, the processor is in communication with both the detector 150 and the light source 140 and can control both of these components. In some embodiments, the processor 160 performs one or more of creating an image of the casted-mono silicon wafer from the detected light and evaluating the crystal fraction of the wafer 120.

The crystal fraction of the wafer can be determined by comparing the area of the wafer with relatively uniform transmission to the area of the wafer with relatively non-uniform transmission. Examples of this can be seen in FIGS. 4 and 5. As used in this specification and the appended claims, the term "uniform transmission" means that the pixel being analyzed is similar in color or intensity to the surrounding pixels within a predetermined threshold. In some embodiments, the image processing finds the grain boundaries (contours) of the largest grain and then calculates the area (based on the number of pixels in the image). In some embodiments, determining the crystal fraction of the casted-mono silicon wafer comprises determining the largest area of the wafer that is mono-crystalline. The percentage of mono-crystalline wafer area can be determined by dividing the mono-crystalline area by the area of the entire wafer. The entire wafer area can be entered directly into the processor by manual input, or can be determined from the vision system.

In some embodiments, the wafer quality can be evaluated based on the percentage of mono-crystalline wafer area. Wafers with a mono-crystalline area greater than about 90% can be indicated as good wafer. Wafers with a mono-crystalline area in the range of about 60% to about 90% can be indicated as seconds or B-grade wafers. Wafers with a mono-crystalline are less than about 60% can be indicates as poor wafers which can be recycled.

Figure 4:
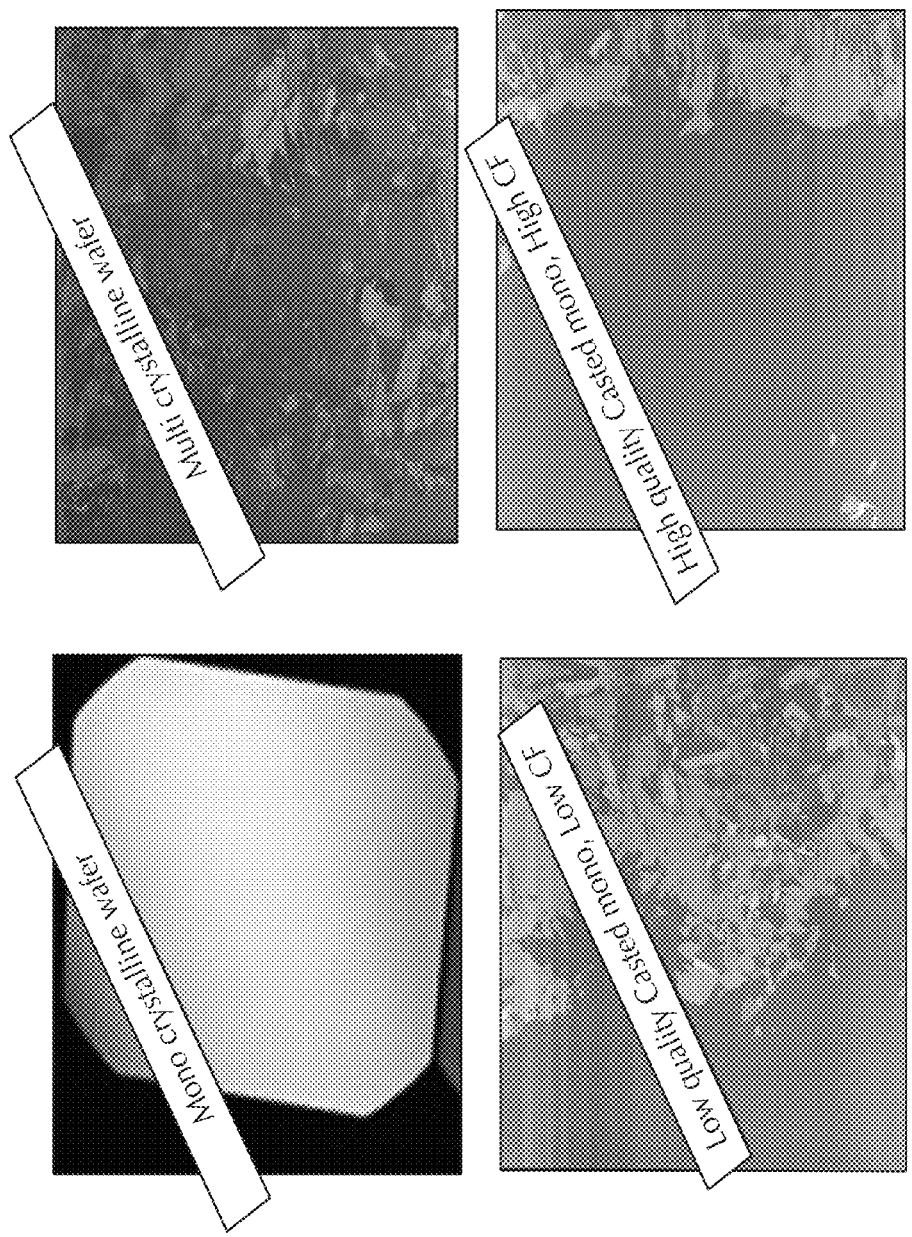
FIG. 4 shows near infra-red images of crystalline silicon solar wafers including mono-crystalline, multi-crystalline and casted-mono wafers.

Referring to FIG. 4, a light emitting diode with a wavelength of 870 nm was directed through a wafer and a line scan camera with a pixel size of 40 micron was placed to monitor the light transmitted through the wafer. The image generated from the camera clearly shows the grain boundaries and the mono and multi crystalline areas. The processor 160 can determine the multi area boundaries and the mono area, to provide a precise and accurate CF measurement. The light budget for the system has been carefully calculated, as the exposure time of the camera has to be extremely short, due to the high production line throughput (commonly 3,600 wafers per hour in high volume production). Due to the high throughput, the cycle time for inspecting the wafers can be very short (e.g., up to 1 second). In some embodiments, the cycle time for inspecting a wafer is up to about 2 second, or up to about 1.5 seconds, or up to about 1 second, or up to about 900 msec, or up to about 800 msec, or up to about 700 msec, or up to about 600 msec or up to about 500 msec. The exposure time of the camera has to be short in order not to get a blurred image. In some embodiments, the exposure time multiplied by the sample velocity should be not more than about 20%, or about 15%, or about 10%, or about 5% of the system resolution. The system resolution of some embodiments if about 60 µm, or about 50 µm, or about 40 µm, or about 30 µm or about 20 µm, or in the range of about 20 µm to about 60 µm.

Figure 5:
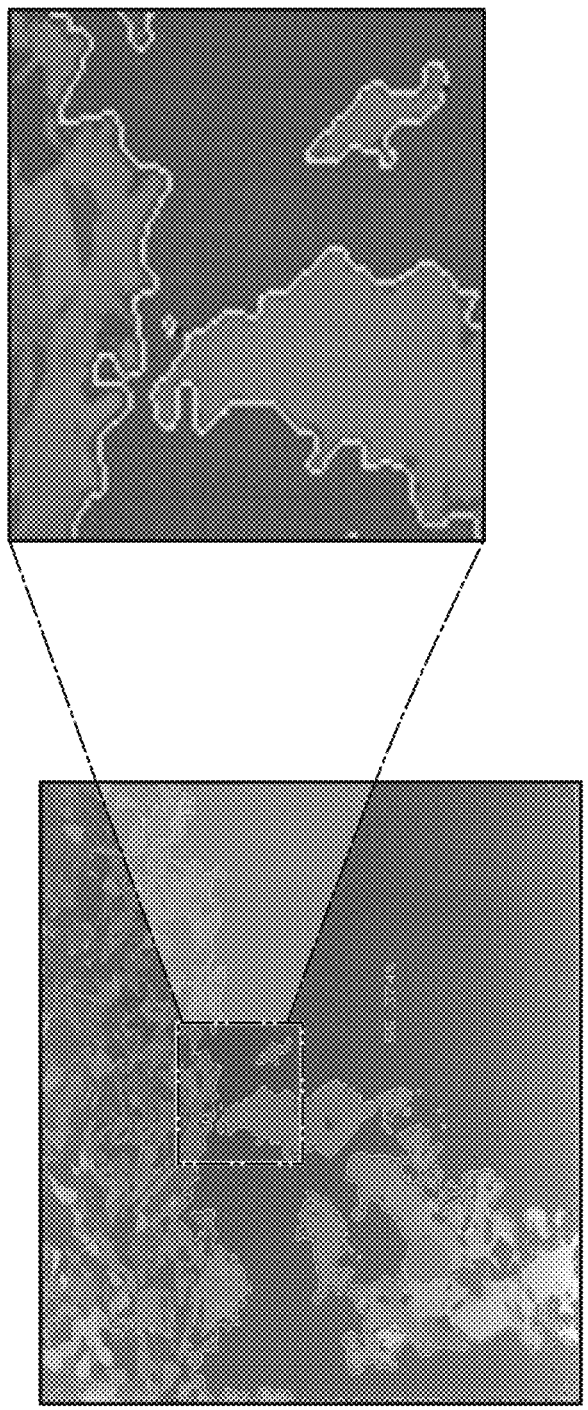
FIG. 5 shows typical casted-mono wafer inspected by the crystal fraction system in accordance with one or more embodiments of the invention.

The inspection system has been built and tested on variety of wafers. A typical wafer image and measured CF are shown in FIG. 5. The contrast obtained at line speed (1 wafer per second) was excellent, giving a clear and crisp image of the grains and their boundaries. With the high quality image obtained, the processor calculates the mono crystal area. The crystal fraction of the wafer shown in FIG. 5 was 55.3%. This wafer would generally be rejected and the silicon recycled for future use.

Figure 6:
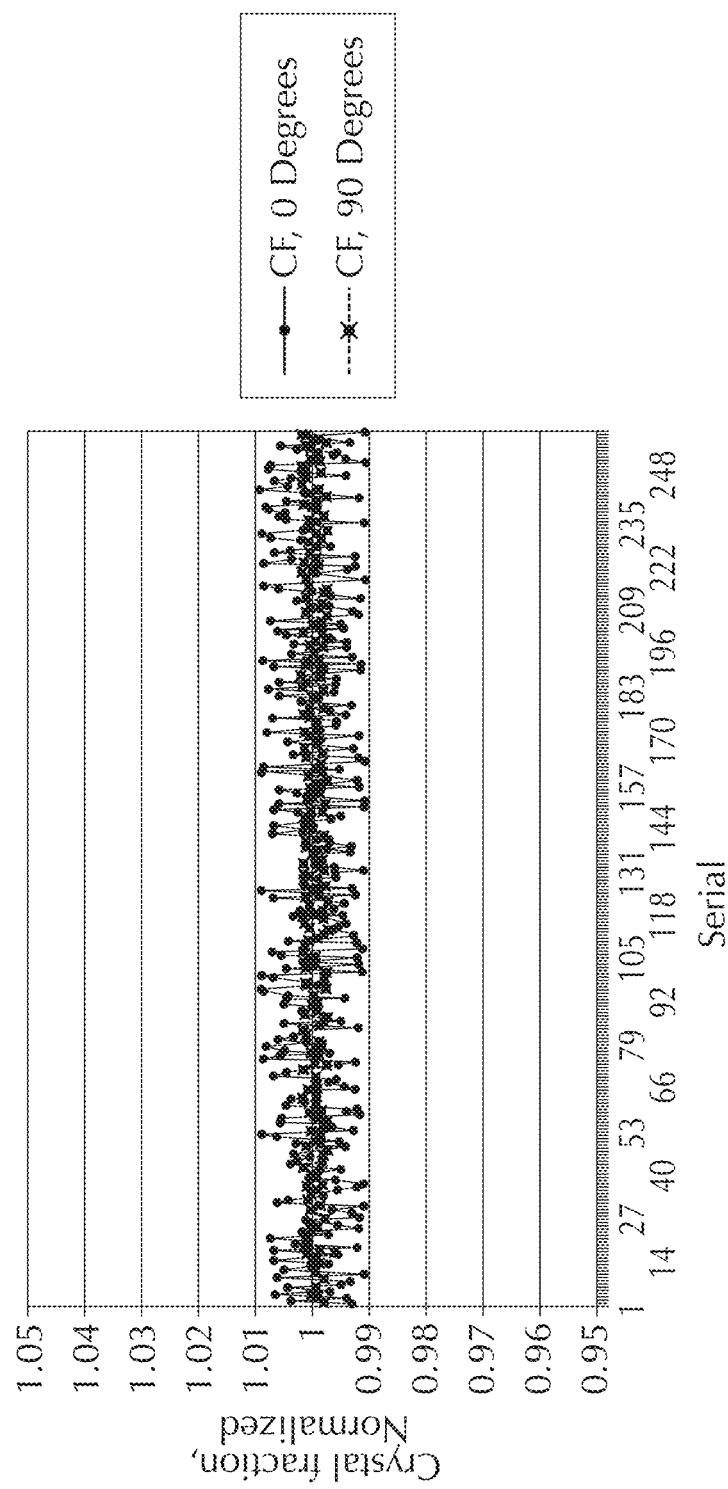
FIG. 6 shows graph of the crystal fraction for repeated measurements for a sample wafer.

To demonstrate the system's repeatability (accuracy and precision), a single wafer was inspected several hundreds of times. Results are shown in FIG. 6. It can be seen that the system demonstrated excellent repeatability (standard deviation of less than 0.2%).

Figure 7:
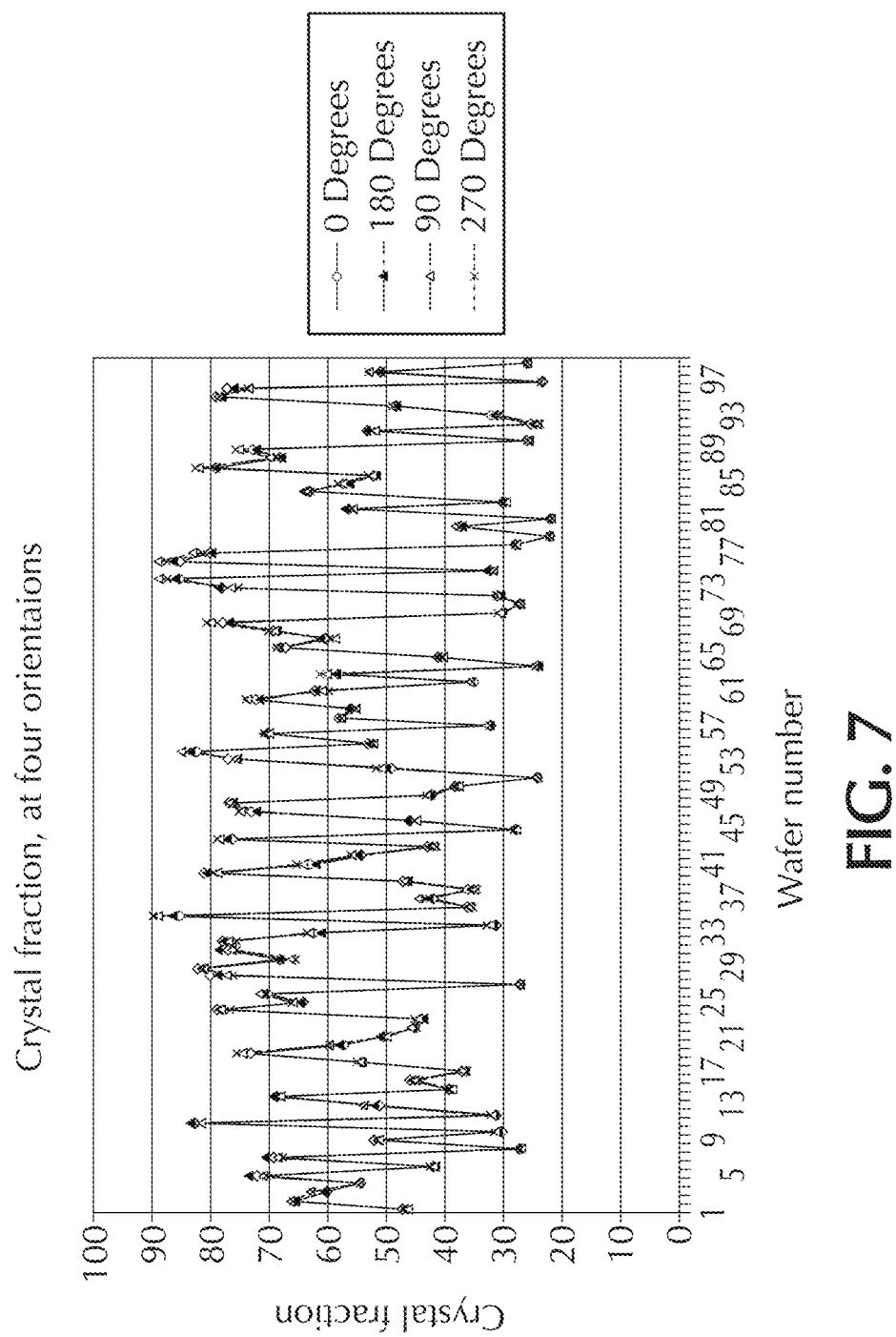
FIG. 7 shows a graph of the crystal fraction for one hundred silicon wafers at multiple orientations.

Since the wafers are roughly square, the invariance to the wafer orientation was tested. One hundred typical wafers were tested in all 4 orientations. The results of which are shown in FIG. 7 and indicated that the measurement is highly invariant to wafer orientation. The measurement error was less than 0.8% peak-to-peak. The variance in CF correlated to a variance of up to 0.7% in efficiency of the produced cells (depending on the process).

The methods and system described provide important information on the wafer's quality, which correlates directly with the cell efficiency. Wafer manufacturers will be able to close loop their production processes and provide higher quality products, as well as, bin their wafers and sell them according to their quality. Cell manufacturers will be able to predict the expected cell efficiency, reject low quality wafers, and better plan their production.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of determining a crystal fraction of a casted-mono silicon wafer, the method comprising:
    passing light through the casted-mono silicon wafer;
    detecting the light that has passed through the casted-mono silicon wafer;
    creating an image of the casted-mono silicon wafer from the detected light; and
    determining the crystal fraction of the casted-mono silicon wafer from the image by determining the largest area of the wafer that is mono-crystalline.

2. The method of claim 1, wherein the light comprises near infrared light.

3. The method of claim 2, wherein the near infrared light has a wavelength of about 870 nm.

4. The method of claim 2, wherein the light is emitted by a light emitting diode (LED).

5. The method of claim 1, further comprising determining a percentage of mono-crystalline wafer area.

6. The method of claim 5, further comprising evaluating the casted-mono silicon wafer quality based on the percentage of mono-crystalline wafer area.

7. The method of claim 6, wherein the casted-mono silicon wafer is evaluated by determining the percentage of the casted-mono silicon wafer that is greater than 90% mono-crystalline to indicates a good wafer, in the percentage range of 60% to 90% to indicate a second grade wafer, and less than 60% mono-crystalline to indicate a poor wafer.

8. A method of determining a crystal fraction of a casted-mono silicon wafer, the method comprising:
    contacting the casted-mono silicon wafer with light;
    detecting the light that has one or more of passed through the casted-mono silicon wafer and reflected off of the casted-mono silicon wafer;
    creating an image of the casted-mono silicon wafer from the detected light; and
    determining the crystal fraction of the casted-mono silicon wafer by determining the largest area of the wafer that is mono-crystalline from the image.

9. The method of claim 8, wherein the light is near infrared light having a wavelength of about 870 nm and is passed through the casted-mono silicon wafer.

10. The method of claim 8, wherein the light is one or more of ultraviolet light, visible light, and infrared light, and is reflected off of the surface of the casted-mono silicon wafer.

11. The method of claim 8, which further comprises calculating a percentage of mono-crystalline wafer area from the image.

12. A system for measuring crystal fraction in casted-mono silicon wafers, the system comprising:
- a support that holds a casted-mono silicon wafer;
- a light source that emits light directed at the casted-mono silicon wafer;
- a detector that measures the light after exposure to the casted-mono silicon wafer; and
- a processor in communication with the detector, that creates an image of the casted mono-silicon wafer from the detected light, wherein the processor evaluates the crystal fraction of the casted-mono silicon wafer by finding a largest mono-crystalline area from the image.

13. The system of claim 12, wherein the light is near infrared light.

14. The system of claim 13, wherein the near infrared light is directed to a back side of the casted-mono silicon wafer and the detector measures near infrared light transmitted through the casted-mono silicon wafer from the light source.

15. The system of claim 13, wherein the near infrared light has a wavelength of about 870 nm.

16. The system of claim 13, wherein the light source is a light emitting diode (LED), and the detector is a CCD Camera that creates the image of the wafer.

17. The system of claim 12, wherein the light is one or more of ultraviolet, visible or infrared light.

18. The system of claim 17, wherein the light is directed to a front side of the casted-mono silicon wafer and the detector measures the light reflected from the front side of the casted-mono silicon wafer from the light source.

19. The system of claim 12, wherein the processor evaluates the crystal fraction of the casted-mono silicon wafer by comparing the area of the wafer with relatively uniform transmission to the area of relatively non-uniform transmission and determining a percentage of uniform to non-uniform area.

* * * * *